United States Patent
Mandeau et al.

(10) Patent No.: US 10,300,102 B2
(45) Date of Patent: *May 28, 2019

(54) EXTRACT OF AERIAL PARTS OF OATS

(71) Applicant: PIERRE FABRE DERMO-COSMETIQUE, Boulogne-Billancourt (FR)

(72) Inventors: Anne Mandeau, Toulouse (FR); Bernard Fabre, Belberaud (FR); Marie-Francoise Aries, Escalquens (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 307 days.

This patent is subject to a terminal disclaimer.

(21) Appl. No.: 15/132,866

(22) Filed: Apr. 19, 2016

(65) Prior Publication Data

US 2016/0228486 A1    Aug. 11, 2016

Related U.S. Application Data

(62) Division of application No. 13/128,650, filed as application No. PCT/EP2009/061972 on Sep. 15, 2009, now Pat. No. 9,339,668.

(30) Foreign Application Priority Data

Nov. 14, 2008  (FR) ...................................... 08 57757

(51) Int. Cl.
| | |
|---|---|
| *A61K 36/899* | (2006.01) |
| *A61K 8/60* | (2006.01) |
| *A61K 8/97* | (2017.01) |
| *A61Q 19/08* | (2006.01) |
| *A61K 8/63* | (2006.01) |
| *A61K 31/7048* | (2006.01) |
| *A61K 45/06* | (2006.01) |

(52) U.S. Cl.
CPC ............ *A61K 36/899* (2013.01); *A61K 8/602* (2013.01); *A61K 8/63* (2013.01); *A61K 8/97* (2013.01); *A61K 31/7048* (2013.01); *A61K 45/06* (2013.01); *A61Q 19/08* (2013.01)

(58) Field of Classification Search
None
See application file for complete search history.

(56) References Cited

U.S. PATENT DOCUMENTS 9,339,668 B2 * 5/2016 Mandeau ............... A61K 8/602
2009/0068128 A1    3/2009 Waddington

FOREIGN PATENT DOCUMENTS

WO    WO 03/066073 A2    8/2003

OTHER PUBLICATIONS

Bahraminejad et al., "Analysis ofthe Antimicrobial Activity of Flavonoids and Saponins Isolated From the Shoots of Oat", Journal of Pathology, vol. 156, No. 1, Jan. 2008, pp. 1-7, XP002532359.
Bieber, "Atopic Dermatitis", The New England Journal of Medicine, Apr. 3, 2008, pp. 1483-1494.
Fowler et al., "Active Naturals Have a Key Role in Atopic Dermatitis", Seminars in Cutaneous Medicine and Surgery, Vo. 27, No. 3, Sep. 1, 2008, pp. 8-10, XP025760163.
Hansel et al., "Hagers Handbook of Pharmaceutical Practice", 5th edition, 1992, pp. 441-445, XP002532360.
Incorvaia et al., "Allergy and the Skin", The Journal of Traniational Immunology, vol. 153, 2008, pp. 27-29.
Lefrancois et al., "Avoine", Internet Article, Jan. 30, 2007, pp. 1-5, http://www.passportsante,net/fr/Solutions/Plantes Supplements/Fiche. aspx?doc=avoine_ps>, XP002532358.
Misery et al., "Sensitive Skin in Europe", European Academy of Dermatology and Venereology, vol. 23, 2008, pp. 373-381.
Spergel, "Immunology and Treatment of Atopic Dermatitis", American Journal of Clinical Dermotol, vol. 9, No. 4, 2008, pp. 233-244.
Wilsmann-Theis et al., "Facing Psoriasis and Atopic Dermatitis: are There More Similarities for More Differences?", European Journal of Dermatol, vol. 18, No. 2, Mar.-Apr. 2008, pp. 172-180.
Fassler, "Developments in Plant Biology", Struct., Funct. Metab. Plant Lipids, vol. 9, 1984, pp. 225-232.

* cited by examiner

*Primary Examiner* — Susan Hoffman
(74) *Attorney, Agent, or Firm* — Birch, Stewart, Kolasch & Birch, LLP

(57) ABSTRACT

The invention relates to an aerial part extract of oats excluding grains, to its preparation method and its uses.

9 Claims, No Drawings

EXTRACT OF AERIAL PARTS OF OATS

This application is a divisional of co-pending U.S. patent application Ser. No. 13/128,650 filed on May 11, 2011, now U.S. Pat. No. 9,339,668, which is the national phase of PCT International Application No. PCT/EP2009/061972 filed on Sep. 15, 2009, which claims the benefit of French Patent Application No. 0857757 filed on Nov. 14, 2008. The entire contents of all of the above applications are hereby incorporated by reference.

The present invention relates to an extract of aerial part of oats preferentially harvested before ear emergence and to its use for treating inflammatory dermatoses.

Oats or *Avena sativa* L. is a yearly plant which may become 1 m 50 tall. On germination, the young plant grows like lawn and then gives several stems with a particular habit of growth. The stem or stubble is hollow, with a diameter of a few millimeters, interrupted from place to place, at the location where the leaves are inserted, through full diaphragms called nodes. The spaces between nodes, first of all very short at the base of the stem, become increasingly longer.

The leaves are alternate, distichous, of a dull blue-green color; they are inserted on the stem at the nodes, through a long forward-slitted sheath which covers almost the whole of the upper intermodal space. The limb is detached therefrom at right angles. It is wide, ribboned, covered with many parallel veins (rectinerves); it is usually pubescent. At the limb where the sheath is detached, a fine membrane expansion of the sheath which is short and truncated, called a ligule, is observed between the stem and the limb.

The stem ends with a large floral panicle spread out in all directions, with a very loose pyramidal shape, all the branches of which end with an elementary inflorescence with a constant structure in the whole family of Poaceae and called spikelet. The spikelets are hanging, relatively large and only comprise two flowers. The spikelet is not born at the axil of a mother bract, but at a short distance from its insertion, it bears two particular opposite bracts, called glumes.

The glumes of oats have a large size; they reach a length of 2 cm and completely envelop the spikelet; they are lanceolated, provided with 7-9 veins and pubescent. The glumellae are small; the external glumella bears a twisted edge, not inserted at the apex but on the back, which exceeds the spikelet by more than one centimeter.

Immediately above the glumellae, the floral axis bears two small not very visible parts, the glumellulae and finely the actual flower which is reduced to three stamens and to three carpels. The stamens, first substantially sessile, then see their net suddenly lengthen upon blossoming, so that the anthers become exserted and hang out of the spikelet. The anthers are inserted on the net through their middle region exclusively, whence their name of medifixed and oscillating anthers. The three carpels form an unilocular ovary, with a style which is divided into very spread-out and feathery stigmatic lobes. All these characters correspond to pollination by wind. There is only one ovule which is anatropic and set upright at the bottom of the ovarian cavity.

The fruit is an achene of a particular type, where the outer foundation will be directly applied against the pericarp. This fruit is called a caryopsis. It is an elongated, tapered, pubescent grain having voluminous amylaceous albumin. The embryo has a very developed cotyledon surrounding the tigella almost completely and separating it from the albumin. The entire embryo is rejected on the side.

The fruit of oats is recognized as a medicinal raw material via an oral route, as a laxative for its ballast effect, but also in the case of cholesterolemia or diabetes of type 2 for its β-glucan content. Via a topical route, the fruit of oats is mainly used as meal, a quality of which, called colloid extract of oats, has a monograph in the United States of Pharmacopoeia USP 22, 1990. This colloidal extract has emollient and softening properties and is defined as the powder resulting from milling and other treatments of the full grain, this quality therefore corresponds to an oat meal. The monograph sets standards of viscosity, microbial limits, desiccation losses, particle size and ash, lipid and nitrogen contents.

From this same portion of the oat, oil used in cosmetology and proteins may also be extracted. The latter which are insoluble, are not directly used but only after enzymatic or chemical hydrolysis. A more or less elaborate hydrolysate is made with which it is possible to obtain either oat peptides with variable molecular weights, or amino acids depending on the force of the hydrolysis. Hydrolyzed oat proteins were examined for their properties in the cosmetic and dermatological fields. Thus, its properties were demonstrated on hair, such as the capability which these peptides have of forming a film on the hair stem, of penetrating into the cuticle and thus by the resulting sheathing effect, of providing a conditioning effect.

With work carried out in vitro on cell cultures, the anti-inflammatory activity of oats colloid extract was able to be evaluated. Thus, this extract has shown inhibitory activity on cutaneous metabolism of arachidonic acid and eïcosanoids, on the expression of cytosolic phospholipase $A_2$ and of cyclooxygenase at a human keratinocyte line, as well an inducing activity of anti-inflammatory cytokine TGFβ1. The cytokines Th1 and Th2 of the immunity cells such as $IL_2$, $IL_4$, $IL_5$, $IL_{13}$, are also controlled by the same colloidal extract. Finally, a clinical study shows the benefit of an oats colloidal extract in a skin irritating model in a double blind skin irritation model and on 12 healthy volunteers.

The external portion of the grain provides the glucans used in dietetics in oat fibres in order to reduce cholesterol level and cardiovascular risks.

The glucans of oats were also investigated for their viscosifying and gelling property as a food supplement.

The glucans extracted from oats also have an immunostimulating activity. Other activities providing value in the cosmetic field have been demonstrated: protection against deleterious effects of UV, stimulation of cell metabolism, stimulation of the synthesis of collagen and improvement of the tensile resistance of hair.

Apart from the grains, oats is used as a fodder plant. Cut when young, it provides much estimated green fodder. The straw is as for it given to horses, cows and sheep, but is not used in human food. In traditional medicine, oat straw is used for preparing baths for soothing rheumatism pains, sciatica and affections of the liver.

In India, ordinary oat decoctions were used for withdrawing addicts from the power of opium. An alcoholic extract prepared from fresh plants was used for tobacco withdrawal with statistically significant results.

Baths based on oat straw or commercial extracts would have as indications: rheumatisms, neuralgia, chronic eczema, neurodermatitis, peripheral vascular disorders . . . .

<<Herbal>> oats is the subject of an EMEA monograph (Ref. EMEA/HMPC/202966/2007) in which mention is made of the use of either dried aerial parts harvested before blossoming, or of a liquid extract (1:5, 45% v/v ethanol) prepared from fresh aerial parts of the harvested plant during the blossoming period.

Traditional use of these aerial parts is described in the case of slight mental stress and for promoting induction of sleep.

From the bibliography, the aerial parts of oats consist of:
Flavonoids:
⇒ C-glycosyl-flavones of the apigenin type (vitexin, isovitexin . . . ) or luteolin (orientin, isoorientin, isoscoparin . . . ),
⇒ O-glycosylated flavones of the tricin type,
⇒ Flavonolignans (salcolins A and B)
Bidesmosidic steroid saponins: Avenacosides A and B (aglycone: nuatigenin)
Proteins
Others: Phenolic compounds (Avenanthramides, hydroxycinnamic acids . . . ), sterols, cerebrosides . . . .

Atopic dermatitis (or atopic eczema) is a frequent dermatological disease, affecting 10-15% of the newborn in France, increasing during the last decades.

Atopic dermatitis is the cutaneous symptom of atopia, this is a chronic inflammatory dermatitis or eczema, occurring on a genetically determined condition, affecting 15-30% of children and 2-10% of adults; its prevalence is in constant increase in industrialized countries, it has doubled or even tripled during the last three decades and is now considered as a major issue of public health. Atopic dermatitis is often associated with other atopic disorders such as allergic rhinitis and asthma. This affection most frequently appears during infancy and is characterized by repeated outbreaks for several years. It develops by eruptions interrupted with spontaneous remissions.

The life quality of patients affected with atopic dermatitis is deeply perturbed; The adopted treatments include corticosteroids and topical immunomodulators, systemic agents, the frequent secondary effects of which limit long term use, emollients. Present therapy is reactive—treatment of the outbreaks—but it is now estimated that an early intervention focused on the control of the eruptions and of the cutaneous inflammation may be beneficial both in terms of controlling the disease and of the possible appearance of asthma and/or rhinitis (BIEBER, T. 2008, *Atopic dermatitis, The New England Journal of Medicine*, Vol 358 (14) 1483-1494), atopic dermatitis being considered as the initial phase of the so-called atopic development. In the majority of the cases, associated local care provides a complement to the treatments used, and provides relief to the patient. There is a significant need for alternative treatments to treatments by corticosteroids.

Atopic dermatitis would be the result of complex interactions between genetic predispositions, environmental factors such as allergens and microorganisms, dysfunction of the skin barrier, dysregulation of the immune system (SPERGEL, J M 2008, *Immunology and treatment of atopic dermatitis, Am J Clin Dermatol*, Vol 9(4) 233-244).

Psoriasis is also a cutaneous inflammatory disease with chronic development; it affects 2% of the population. With atopic dermatitis, these are the most frequent chronic inflammatory diseases of the skin. It is characterized by an abnormal growth of epidermal cells associated with an inflammatory reaction. The central mechanism of this inflammation phenomenon is related to the action of the T cells of the immune system, predominantly cells of the Th1 type (WILSMANN-THEIS, D.; HAGEMANN, T.; JORDAN, J.; BIEBER, T.; NOVAK, N. 2008, *Facing psoriasis and atopic dermatitis: are there more similarities or more differences?, Eur J Dermatol*, Vol 18 (2) 172-180) which initiate and sustain the inflammatory process and stimulate excessive proliferation of keratinocytes which then undergo an accelerated and incomplete differentiation phase. Keratinocytes express receptors which make them sensitive to the inflammatory signals and release pro-inflammatory mediators. Psoriasic inflammation is thus sustained by mutual stimulation of the T cells and of the keratinocytes.

The disease has therefore to be treated in the long term.

There thus exists a need and a strong demand for therapeutic alternatives to these inflammatory dermatoses.

Unexpectedly and surprisingly, the inventors have shown new ways of adding value to an extract of aerial parts of oats in therapeutic and cosmetic/dermatology. Advantageously, said extract has immunomodulating and anti-inflammatory properties useful in the treatment of atopic dermatitis. The extract according to the present invention has also shown good capacities for treating acne and skin ageing.

The object of the present invention is thus an extract of aerial part(s) of oats, excluding grains, characterized by 2-15% of flavonoids and 0.2-2% of avenacosides A and B.

By aerial parts of oats, is meant in the sense of the present invention any portion of the oat plant located above the ground, excluding the grains.

Preferably, the aerial parts of oats comprise the leaves and/or stems and/or spikelets and/or flowers.

The obtained oat extract is characterized by its content of flavonoids and of saponins of interest. The latter are analyzed by high pressure liquid chromatography, by two different methods suitable for each type of compounds.

The contents of these different molecules vary depending on the extraction conditions. The main flavonoids are isovitexin-2"-O-arabinopyranoside and isoorientin-2"-O-arabinopyranoside. The avenacosides A and B are the main saponins. These are bisdesmosidic steroid saponins.

Advantageously, the extract according to the invention comprises a proportion of 5-10% of the main flavonoids: isovitexin-2"-O-arabinopyranoside and isoorientin-2"-O-arabinopyranoside.

Advantageously, the extract according to the invention is an extract obtained in an organic solvent.

Advantageously, the extract according to the invention comprises less than 1 ppm of proteins, preferentially less than 0.5 ppm and still more preferentially less than 0.3 ppm of proteins.

Advantageously, the extract according to the invention is an extract of aerial parts of oats harvested before ear emergence.

In the sense of the present invention, <<aerial parts of oats harvested before ear emergence>> designate the aerial parts of oats harvested after germination (about 2 weeks to 2 months after germination) during the stem elongation stage right up to ear emergence, not included.

In the sense of the present invention, <<stem elongation>> designates the growth phase which corresponds to elongation of the stem and to the emergence of the forming ear, before blooming.

Another object of the present invention is a method for preparing an extract of aerial part(s) of oats, said aerial part(s) not comprising any grains, comprising the following steps:
drying and milling of the aerial part(s) of oats,
extraction in an organic solvent selected from the group consisting of ketones, esters, $C_1$-$C_4$ alcohols, and miscible mixtures in any proportion of these solvents, and centrifugation or filtration.

Advantageously, the organic solvent of the method according to the invention is selected from the group consisting of acetone, methylethylketone, methylisobutylketone, ethyl acetate, a $C_1$-$C_4$ alcohol and a mixture in any miscible proportion of these solvents.

Advantageously, the aerial part is harvested after 2 months, at the end of the elongation but before ear emergence, and then dried and milled.

The extraction is carried out under stirring or in a static way.

Extraction is carried out with reflux or at room temperature.

Advantageously, extraction is carried out in a plant/solvent ratio which may vary from 1/7 to 1/20, preferably from 1/8 to 1/12.

Preferentially, extraction is carried out for a period of 30 minutes to 48 hours, more preferably from 60 to 120 minutes.

Extraction may be renewed 2 or 3 times.

The pomace obtained by the extraction step is then separated from the extract by centrifugation or filtration and the solution may be more or less concentrated until a dry extract is obtained.

A discoloration treatment may be carried out either with delipidation by concentration, precipitation and filtration, or by adding to the extracted solution either concentrated or not an absorbing support such as active coal or an adsorbing resin.

A support may be added during the drying step in mass proportions relatively to the extracted dry material which may vary from 1 to 75%. The support may be a sugar such as maltodextrin, lactose, silica or any other cosmetologically acceptable support.

Another object of the present invention is an extract of oat aerial parts excluding grains, capable of being obtained by the method according to the invention.

Advantageously, this extract is obtained by extraction with acetone or acetone/water up to 20% of water.

An extract of the acetone or acetone/water type with up to 20% of water, includes the molecules of interest, flavonoids and saponins, and is very considerably depleted in proteins. Indeed, the methods for dosing proteins described in the European. Pharmacopoeia do not produce any result, and migration on a SDS-Page gel by electrophoresis after precipitation from acetone and disclosure with Coomassie's blue or with silver nitrate shows the absence of any band signaling the presence of protein. By depositing a control on this same electrophoresis it is possible to quantify the protein detection limit to 1 ng, this extract therefore has a protein content less than 1 ppm (reduced to the amount of extract deposited on the gel). Preferentially, said protein content is less than 0.5 ppm and even more preferentially less than 0.3 ppm of proteins.

Another object of the present invention relates to a dermatological or cosmetic composition comprising an extract according to the invention and one or more either dermatologically or cosmetologically acceptable excipients, respectively.

The composition according to the invention may in particular contain additives and formulation aids such as emulsifiers, thickeners, gelling agents, water fixatives, spreading agents, stabilizers, coloring agents, perfumes and preservatives.

The cosmetic or dermatological composition according to the invention further comprises usual dermatologically compatible excipients.

Preferentially, the composition according to the invention comprises an amount of extract of aerial part(s) of oats, as an active ingredient, comprised between 0.1 and 5% by weight based on the total weight of the composition.

Advantageously, said amount of extract is comprised between 0.1% and 0.5% by weight, based on the total weight of the composition.

The dermatological or cosmetic composition according to the present invention may be prepared as a water-in-oil (W/O) emulsion or oil-in-water (O/W), as a multiple emulsion such as for example a water-in-oil-in-water (W/O/W) or an oil-in-water-in-oil (O/W/O) emulsion, a micro-emulsion or even as a hydrodispersion or lipodispersion, a gel or an aerosol.

The dermatological or cosmetologically compatible excipients may be any excipient among those known to one skilled in the art in order to obtain a composition for a topical application as a milk, cream, balm, oil, lotion, gel, foaming gel, unguents, spray, etc.

Another object of the present invention relates to an extract according to the invention for use as a drug.

Another object of the present invention relates to an extract according to the invention for use in the treatment of inflammatory dermatoses.

Another object of the present invention relates to an extract according to the invention for use in the treatment of atopic dermatitis, psoriasis or eczema which are inflammatory dermatoses.

Another object of the present invention relates to the use of an extract according to the invention for preparing a drug intended for treatment of inflammatory dermatoses.

Another object of the present invention relates to the use of an extract according to the invention for preparing a drug intended for the treatment of atopic dermatitis, psoriasis or eczema which are inflammatory dermatoses.

Another object of the present invention relates to an extract according to the invention for use in the treatment of acne or skin aging.

Another object of the present invention relates to the use of an extract according to the invention in a cosmetic and/or dermatological composition intended for the treatment of acne or skin aging.

Another object of the present invention relates to an extract according to the invention for use in the treatment of rosacea.

Another object of the present invention relates to the use of an extract according to the invention in a cosmetic and/or dermatological composition intended for treatment of rosacea.

Rosacea is an inflammatory and chronic disease of the skin of the face. This is an incurable most often benign skin disease, which is expressed by chronic red patches at the nose, the cheeks, sometimes also at the chin, and at the forehead.

Another object of the present invention relates to an extract according to the invention for use in the treatment of sensitive skins.

Another object of the present invention relates to the use of an extract according to the invention in a cosmetic and/or dermatological composition intended for treatment of sensitive skins.

By sensitive skin, is meant in the sense of the present invention, skins with increased sensitivity. Sensitive skin or reactive skin is a syndrome characterized by neurosensitive signs such as an inflammation, itching, smarting. Among the clinical signs resulting from the clinical evaluation of dermatologists, are found: erythema, edema, dryness/desquamation, papules/vesicles, acne lesions (L. Misery et al., *JEADV* 2009, 23, 376). Sensitive skins are hyper-reactive skins which require the use of well-tolerated hygiene and care products. Sensitive individuals are persons who particularly react to aggressions more rapidly than the skin of the majority of other persons.

The following examples illustrate the invention without limiting the scope thereof.

EXAMPLE 1

Preparation of an Extract of Aerial Parts of Oats Harvested Before Ear Emergence According to the Invention a. By Acetone Extraction 400 kg of dried aerial parts of oats harvested before ear emergence are milled and then placed in a reactor with 10 volumes of the acetone/water mixture, under stirring for one hour at room temperature.

By solid/liquid separation, it is possible to obtain a first extraction juice. The pomace is extracted a second time with 10 volumes of the acetone/water mixture for one hour at room temperature, under stirring. By solid/liquid separation, it is possible to obtain a second extraction juice which is gathered with the first. The obtained solution is concentrated on water to 1.33 volumes/kg and then filtered. The thereby obtained extract is dried by microwaves after adding a maltodextrin support (qsp 25%/native extract).

Thus, 36 kg of a pale brown powder are obtained with a titer of 6% of flavonoids (isovitexin-2"-O-arabinopyranoside and isoorientin-2"-O-arabinopyranoside) and of 0.6% of avenacoside B and the protein content of the thereby obtained extract is less than 0.3 ppm.

b. By Ethanol Extraction

Extraction of 100 g of dried and milled plants with an ethanol/water 50:50 mixture for one hour with reflux, solid/liquid separation and evaporation in vacuo at 50° C. 26 g of extract are thereby obtained as a brown powder, with a titer comprised between 1.5 and 3% of flavonoids (isovitexin-2"-O-arabinopyranoside and isoorientin-2"-O-arabinopyranoside).

EXAMPLE 2

Biological Study of the Extract of Aerial Parts of Oats Harvested Before Ear Emergence from Example 1.a The pharmacological study of the extract of aerial parts of oats deals with the immuno-inflammatory component of atopic dermatitis. Alteration of the epidermal barrier (notably mutation of the gene of filaggrin) facilitates penetration of the allergens of high molecular weight (from mites, pollens, . . . ), their capture by dendritic cells and their presentation to the T cells; this interaction leads to a T cell response at the skin—initially Th2 with production of a panel of pro-inflammatory cytokines and chemokines capable of maintaining the inflammation: IL-4, IL-5, IL-13 associated with atopic dermatitis, with significant emergence of IL-17 and IL-31—but more belatedly Th1 (INCORVAIA, C.; FRATI, F.; VERNA N.; D'ALO, S.; MOTOLESE, A.; PUCCI, S. 2008, *Allergy and the skin, Clin Exp Immunol*, Vol 153 (1) 27-29); (BIEBER, T. 2008, *Atopic dermatitis*, The *New England Journal of Medecine*, Vol 358 (14) 1483-1494). The activation of T lymphocytes is followed by the activation of other cell types, mainly keratinocytes and endothelial cells, which results in the production of inflammatory mediators (cytokines, prostaglandins) and in the production of chemokines allowing recruitment of inflammatory cells.

a. Preparation of the Fractions:

The extract of aerial parts of oats may be fractionated in order to identify the class of molecules or the molecules responsible for the activity.

For this, the extract may be deposited on a medium pressure silica column and successively eluted with solvents of increasing polarity, for example an increasing concentration of methanol in water. Indeed, fractionation obtained after depositing the extract made according to Example 1.a on a silica column and first eluting it with a methanol/water mixture from 25:75 to 50:50 and then to 100% methanol made it possible to separate a flavonoid-rich fraction (50:50 methanol/water fraction, 19% of flavonoids isovitexin-2-O-arabinopyranoside and isoorientin-2-O-arabinopyranoside expressed as vitexin-2-arabinose) and a saponin-rich fraction (fraction with 100% methanol, 15% of avenacoside B). From the first fraction the flavonoids isovitexin-2-O-arabinopyranoside and isoorientin-2-O-arabinopyranoside were isolated by semi-preparative HPLC using a C-18 reverse silica column, including structures which were confirmed by mass spectrometry and nuclear magnetic resonance.

Avenacoside A and avenacoside B were isolated from the saponin-rich fraction by semi-preparative HPLC, including structures which were identified by mass spectrometry and nuclear magnetic resonance.

b. Immunomodulating Activity

Cytokines, which represent a vast set of regulatory proteins of the immune system, are produced by resident or infiltrated skin cells, activated during inflammatory or immune processes.

The interleukins including $Il_2$, $Il_4$, $Il_5$ and $Il_{13}$, produced by the lymphocytes are divided into two groups: the cytokines of type Th1 including $Il_2$ and the cytokines of type Th2 including $Il_4$, $Il_5$ and $Il_{13}$. All these interleukins are overproduced during inflammatory pathologies such as atopy, contact eczema or psoriasis.

Among them, human interleukin 2 (IL-2), derived from T cells, is capable of sustaining proliferation of activated T lymphocytes and induces processes for differentiation and activation of B and NK (Natural Killer) cells.

In vitro, human mononucleated cells may be stimulated and produce cytokines. The principle of this test is to study the influence of the extracts on the productions of $IL_2$, $IL_4$, $IL_5$, $IL_{13}$ induced by dual stimulation Phorbol Myristate Acetate/Ionomycin.

Results:

An acetone extract of aerial parts of oats harvested before ear emergence according to Example 1.a inhibits by 52% the number of CD4 lymphocytes expressing interleukin 2 and by 21% the intracellular $IL_2$ level at the concentration of 30 μg/ml. This same extract at the concentration of 30 μg/ml inhibits lymphocyte productions of interleukin 4 by 51%, of interleukin 5 by 31% and interleukin 13 by 78%.

This activity interesting for treating atopic dermatitis is conveyed by the saponins of the extract, including the avenacosides A and B.

c. Anti-Inflammatory Activity

Principle:

The keratinocyte, the most represented cell at the epidermis, plays a significant role in initiating and modulating inflammatory reactions of the skin. With the model it is possible to determine in vitro the capabilities of various molecules of modulating the production of mediators stemming from the metabolism of arachidonic acid. Prostaglandin PG6KF1α is a stable metabolite of prostacyclin. PGI2, a major metabolite produced by the stimulated human keratinocyte. An acetone extract of aerial parts of oats harvested before ear emergence and its fractions were evaluated on the production of this prostaglandin induced at the keratinocyte by the calcium ionophore A23187 (stimulating the cascade of arachidonic acid).

Results:

The acetone extract according to Example 1.a has significant activity (40% inhibition at 0.1 µg/ml), and the flavonoid-rich fraction has significant activity with a maximum of 49% inhibition at 10 µg/ml.

This anti-inflammatory activity is conveyed by the flavonoids present in the extract, and in particular by isoorientin-2″-O-arabinosyl (55% inhibition at 10 µg/ml).

The action mechanism of this inhibition of the release of prostacyclin was partly elucidated: direct inhibition in vitro of cyclooxygenase 2 by the acetone extract (68% inhibition at 100 µg/ml) is observed, and no inhibition of phospholipase A2.

d. Anti-Oxidant Activity

The anti-radical activity of an extract of aerial parts of oats prepared according to Example 1.a, is evaluated with the DPPH● (2,2'-diphenyl-1-picrylhydrazyl) test. This fast test easy to apply is based on the measurement of the trapping capacities of the stable free radical DPPH●. The free radical DPPH● which absorbs at 517 nm, is reduced into corresponding hydrazine when it reacts with the proton donors:

R—OH+DPPH●R—O●+DPPH$_2$

The IC$_{50}$ corresponds to the concentration of the extract causing 50% reduction in the absorbance of a methanol solution of DPPH● (C=25 µg/ml).

Under these conditions, vitamin E has an IC$_{50}$ of 6-10 µg/ml and the acetone extract of aerial parts of oats before emergence an IC$_{50}$ of 70 µg/ml.

This extract therefore has an anti-oxidant activity, and may therefore be used in a dermocosmetic formulation as an anti-ageing agent.

e. Anti-Microbial Activity

The acetone extract prepared according to Example 1.a has selective action on the germ implied in acne, *Propionibacterium acnes*—(see Table 1).

TABLE 1

Minimum inhibitory concentrations expressed as a percentage (w/w) of an acetone extract of aerial parts of oats according to Example 1.a of different germs, Gram +, Gram − bacteria, yeasts and fungi.

| Germs | MIC |
| --- | --- |
| *Staphylococcus aureus* | ≥3.07% |
| *Staphylococcus epidermidis* | ≥3.07% |
| *P. acnes* | 0.096% |
| *Pseudomonas aeruginosa* | ≥3.07% |
| *Escherichia coli* | ≥3.07% |
| *Candida albicans* | ≥3.07% |
| *Aspergillus niger* | ≥3.07% |
| *M. furfur* | ≥3.07% |

EXAMPLE 3

Compositions According to the Present Invention

Emollient Cream for Atopic Skins

| | |
| --- | --- |
| Extract of aerial parts of oats (Ex. 1.a) | 0.1-0.5% |
| Mineral oil | 10-20% |
| Evening primrose oil | 2.5% |
| Cyclomethicone | 5-8% |
| Glyceryl stearate/PEG-100 stearate | 5% |
| Glycerin | 5% |
| Polyacrylamide & C13-14 isoparaffin & laureth-7 | 3% |
| PEG-12 | 4% |
| EDTA | 0.2% |
| Triethanolamine | 0.1% |
| Preservatives | qs |
| Water | qsp 100% |

Moisturizing Milk for Atopic Skins

| | |
| --- | --- |
| Extract of aerial parts of oats (Ex. 1.a) | 0.1-0.5% |
| Mineral oil | 3% |
| Vaseline | 6-12% |
| Dimethicone | 2% |
| Evening primrose oil | 2.5% |
| Sorbitan stearate/sucrose cocoate | 5% |
| Xanthan gum | 0.4% |
| Carbomer | 0.2% |
| Triethanolamine | 0.1% |
| Glycerin | 3% |
| EDTA | 0.2% |
| Behenic alcohol | 1% |
| Preservatives | qs |
| Water | qsp 100% |

What is claimed is:

1. A method for preparing an extract of aerial part(s) of oats harvested two weeks to two months after germination during the stem elongation stage and before ear emergence, said extract comprising a proportion of 2 to 15% of flavonoids and 0.2 to 2% of avenacosides A and B, said method comprising the following steps:
   extraction in an organic solvent selected from the group consisting of acetone, acetone/water up to 20% water, and ethanol/water in proportion 1:1, and
   centrifugation or filtration.

2. A method of treating inflammatory dermatoses, which comprises administering to a patient in need there of an effective amount of the extract obtained by the method according to claim 1.

3. The method according to claim 2, the inflammatory dermatosis being atopic dermatitis, psoriasis or eczema.

4. A method of treating acne, which comprises administering to a patient in need thereof an effective amount of the extract obtained by the method according to claim 1.

5. A method of treating skin ageing, which comprises administering to a patient in need thereof an effective amount of the extract obtained by the method according to claim 1.

6. A method of treating rosacea, which comprises administering to a patient in need thereof an effective amount of the extract obtained by the method according to claim 1.

7. A method of treating reactive skin, which comprises administering to a patient in need thereof an effective amount of the extract obtained by the method according to claim 1.

8. The method according to claim 1, wherein said extract comprises a proportion of 5 to 10% of flavonoids, isovitexin-2"-O-arabinopyranoside, and isoorientin-2"-O-arabinopyranoside.

9. The method according to claim 1, wherein said extract comprises less than 1 ppm of proteins.

\* \* \* \* \*